United States Patent [19]
Ihara et al.

[11] Patent Number: 5,255,557
[45] Date of Patent: Oct. 26, 1993

[54] APPARATUS FOR TESTING A TUBE FOR ITS STRENGTH TO RESIST INTERNAL PRESSURE

[75] Inventors: Chikashi Ihara; Michio Sekiguchi, both of Nagoya, Japan

[73] Assignee: NGK Insulators, Ltd., Nagoya, Japan

[21] Appl. No.: 853,614

[22] Filed: Mar. 18, 1992

[30] Foreign Application Priority Data

Mar. 20, 1991 [JP] Japan .................. 3-081786

[51] Int. Cl.⁵ .......................................... G01M 3/02
[52] U.S. Cl. ............................................ 73/37; 73/49.2
[58] Field of Search ..................... 73/37, 49.2, 49.5

[56] References Cited

U.S. PATENT DOCUMENTS

| 3,895,514 | 7/1975 | Northup | 73/49.4 |
| 4,838,073 | 6/1989 | Jansch | 73/49.2 X |

FOREIGN PATENT DOCUMENTS

| 0002140A1 | 5/1979 | European Pat. Off. | |
| 0454371A2 | 10/1991 | European Pat. Off. | |
| 143429 | 11/1980 | Japan | 73/37 |
| 953509 | 8/1982 | U.S.S.R. | 73/49.5 |
| 1531557 | 11/1978 | United Kingdom | |
| 2149126 | 6/1985 | United Kingdom | 73/37 |
| 2177220 | 1/1987 | United Kingdom | 73/37 |

Primary Examiner—Hezron E. Williams
Assistant Examiner—Joseph W. Roskos
Attorney, Agent, or Firm—Shea & Gould

[57] ABSTRACT

An apparatus for testing a tube for its strength to resist internal pressure, is composed of: an expandable elastomer having a hollow body with one open end; a test head, connected to the expandable elastomer, to provide the expandable elastomer with pressure using fluid as a medium; a holder, disposed below the test head, to vertically move a tube into a place in which the expandable elastomer is inserted into a tube; and a transferring mechanism, arranged beside the holder, to provide the holder with a tube from a rack. The apparatus according to the present invention can automatically and continuously test numerous tubes for its strength to resist internal pressure, overcoming disadvantages of the non-automatic, non-continuous apparatus previously disclosed.

3 Claims, 4 Drawing Sheets

APPARATUS FOR TESTING A TUBE FOR ITS STRENGTH TO RESIST INTERNAL PRESSURE

BACKGROUND OF THE INVENTION

1. Field of the Invention

This invention relates to an apparatus for testing a tube for its strength to resist internal pressure. Though various tubes can be tested in the apparatus according to the present invention, a $\beta$-aluminum tube, which may be used as a solid electrolyte in a sodium-sulfur cell, is particularly suited to be tested in the apparatus according to the present invention.

2. Description of the Prior Art

To test the strength of a $\beta$-aluminum tube to resist internal pressure, one method has been known in which the open end of a tube is tightly contacted to a head that provides pressurized water, and then pressurized water is poured into the tube. A tube that does not stand a specific pressure is destroyed. This method, however, has a disadvantage that it takes considerable time and cost to dry the tubes that pass the test.

To overcome this disadvantage, an apparatus for testing a tube for its strength by expanding an elastomer up to a specific pressure inside a tube to be tested, has been disclosed by the present applicants in Japanese Utility Model Application Laid Open No. 1-97241 (1989). In this apparatus it is necessary to cover an elastomer by a tube one after one by hand, and it is highly inconvenient to test numerous tubes continuously. Moreover, when an elastomer expands inside a tube to be tested in this apparatus, sometimes the tube is not pushed evenly but to one direction, and an area close to the open end of the tube gets contacted with a metallic part outside the tube in the apparatus to result to scratches and damages in the area of the tube.

SUMMARY OF THE INVENTION

According to the present invention, there is provided an apparatus for testing a tube for its strength to resist internal pressure, comprising: an expandable elastomer having a hollow body with one open end; a test head connected to the expandable elastomer to provide the expandable elastomer with pressure using fluid as a medium; a holder disposed below the test head to vertically move a tube into a place in which the expandable elastomer is inserted into a tube; and a transferring mechanism arranged beside the holder to provide the holder with a tube from a rack.

According to another aspect of the present invention, the apparatus further comprises a plastic sheet connected to the test head surrounding an upper part of the expandable elastomer.

According to another aspect of the present invention, the apparatus further comprises a rotary table that is connected to at least two test heads with expandable elastomers, whereby a test head with an expandable elastomer can be replaced with another test head with an expandable elastomer.

BRIEF DESCRIPTION OF THE DRAWINGS

Further details are explained below with the help of the examples illustrated in the attached drawings.

DESCRIPTION OF THE PREFERRED EMBODIMENT

Figure 1:
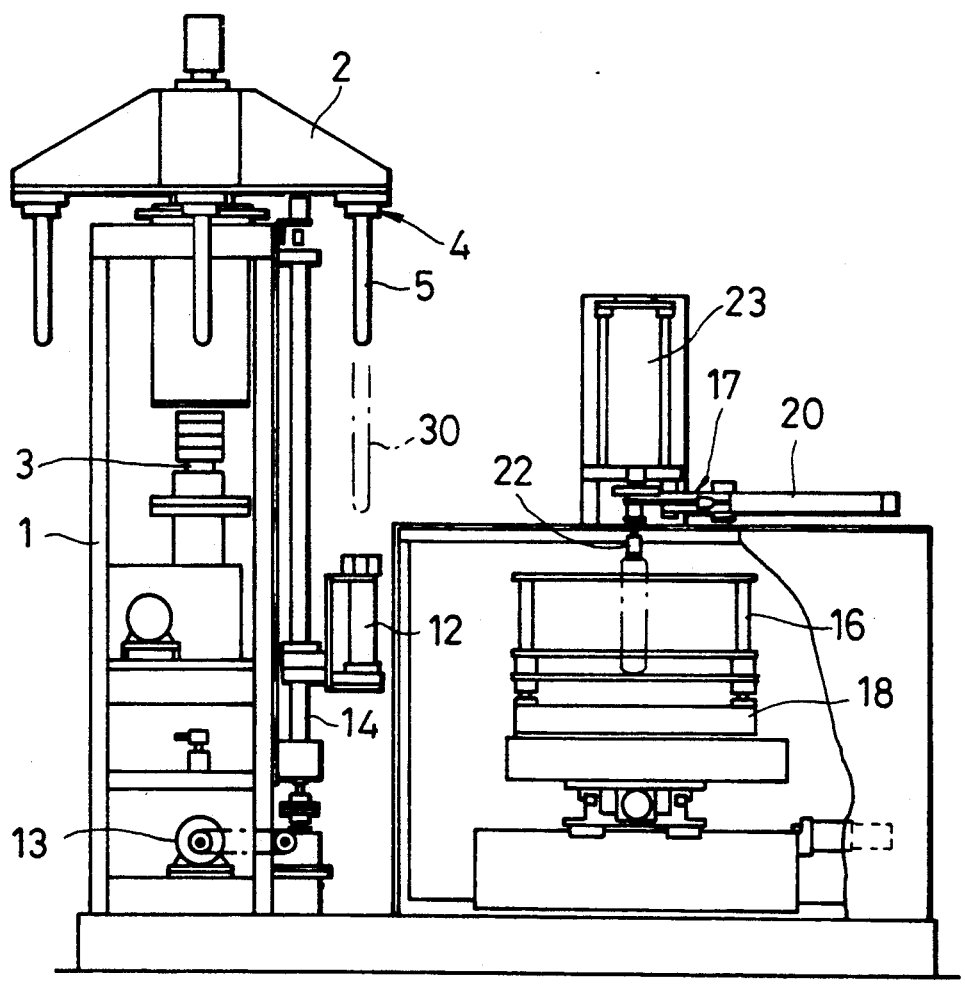
FIG. 1 is a front view of the apparatus according to the present invention.
Figure 2:
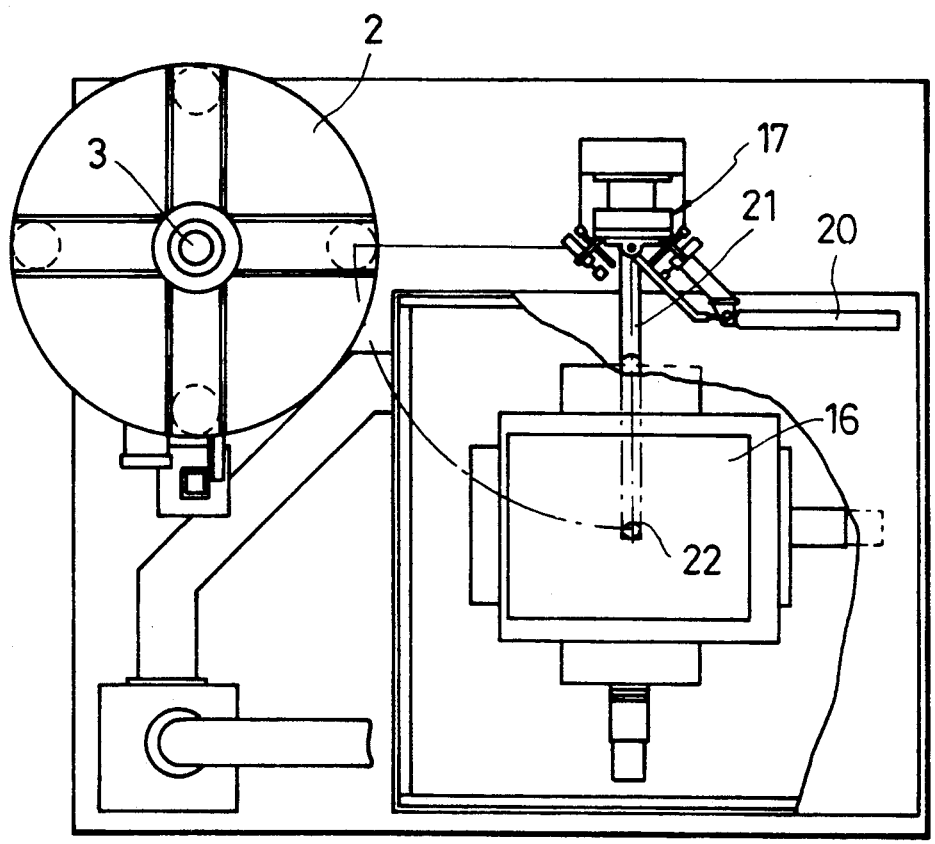
FIG. 2 is a top view of the apparatus according to the present invention.

In FIGS. 1 and 2 the frame of the main body is designated as 1; a rotary table 2 that rotates around a vertical shaft 3 is disposed above the frame 1; and four test heads are connected to the rotary table 2 so that they have a $C_4$ symmetry with its rotation axis overlapping the vertical shaft 3. In FIG. 1 the position where the test head 4 in the right side of the rotary table 2 is located is referred to as the test position, and the other three test heads 4 are located at waiting positions. In this configuration a test head 4 in a waiting position can promptly replace the test head 4 in the test position by rotating the rotary table 2 when, for example, the test head 4 in the test position wears out.

Figure 3:
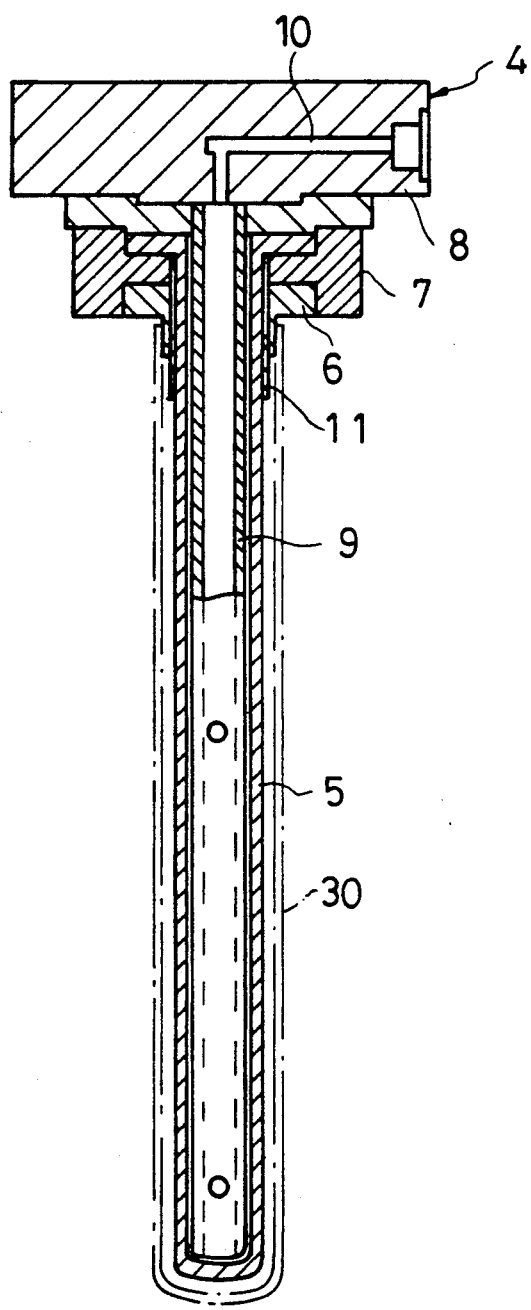
FIG. 3 is a cross section of a test head with an expandable elastomer.

As shown in FIG. 3 a test head 4 includes a head's main body 8, a metallic part 6, and a metallic fitting 7. A head's main body 8 contains an open cavity 10 to provide an expandable elastomer 5 with pressurized fluid.

An expandable elastomer 5, which has a hollow body with one open end, is attached to the head's main body 8 by the metallic part 6 and the metallic fitting 7 so that the hollow space of the expandable elastomer 5 is connected to the open cavity 10 in the head's main body 8 through a rigid tube disclosed below. In this application an expandable elastomer 5 has a shape like a slender balloon or a tube to accommodate a tube 30 to be tested. However, the shape and the size of an expandable elastomer 5 can be modified according to a sample to be tested.

A rigid tube 9 having at least one hole is disposed inside an expandable elastomer 5, and the open end of the rigid tube 9 is connected to an open cavity 10 in a head's main body 8. After a tube 30 shown in a broken line in FIG. 3 covers over an expandable elastomer 5, pressurized fluid provided by the open cavity 10 in the head's main body 8 fills the inside of the expandable elastomer 5 through holes of the rigid tube 9 to expand the expandable elastomer 5 and to exert a specific internal pressure to the tube 30. Water is a preferable fluid as a medium to produce pressure.

During a test a tube 30 is sometimes damaged in an area close to the open end by being pushed into one direction due to uneven expansion of an expandable elastomer 5. To prevent such the damage the inner side of a metallic part 6 is extended downward to some extent, and a plastic sheet 11 is inserted into the space between the extended part of the metallic part 6 and the expandable elastomer 5. The plastic sheet 11 prevents the upper part of expandable elastomer 5 covered by the sheet from uneven expansion, and thus it prevents potential damage in an area close to the open end of a tube 30.

Figure 4:
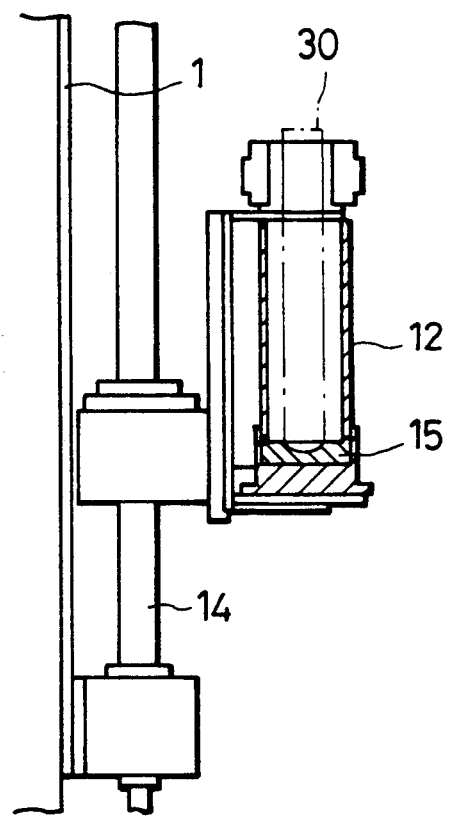
FIG. 4 is a front view of a holder and nearby parts. The shaded portion designates a cross section.

As shown in FIG. 1, the apparatus according to the present invention contains a holder 12 for vertical motion that carries a tube 30 upward and downward, and it also makes a tube 30 contact with the test head 4 in the test position. This holder 12 operates by a feed screw 14 driven by a motor 13. As shown in FIG. 4, a holder 12 contains a tube-like structure with a rubber member 15 in its bottom, and this rubber member 15 supports a tube 30 without damaging it. The structure of a holder 12 can be modified according to the shape and the size of a sample to be tested. Moreover, when a tube 30 with low strength is broken during a test, this holder 12 also functions to prevent broken pieces from scattering.

Figure 5:
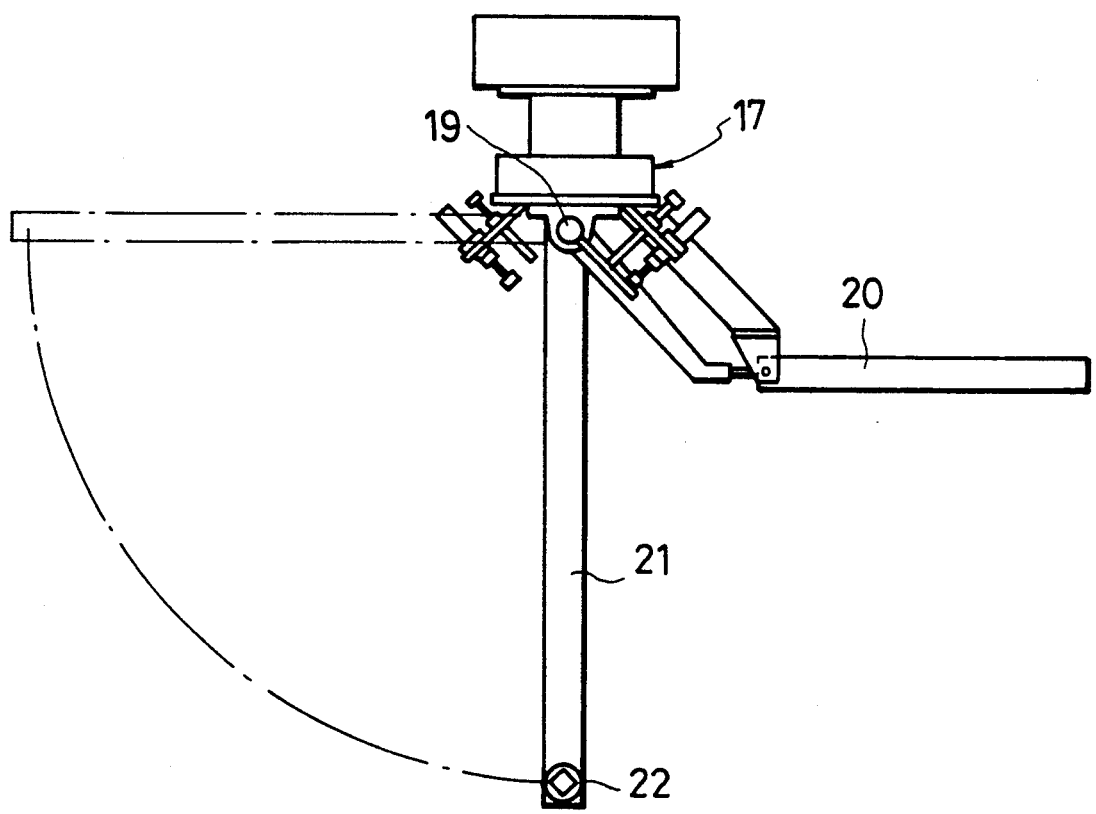
FIG. 5 is a top view of a transferring mechanism.

As shown in FIGS. 1 and 2, adjacent to a holder 12 a rack 16 is disposed that arranges a plurality of tubes 30 and a transferring mechanism 17 that picks up a tube 30 to provide a holder 12 with a tube 30 one by one. The rack 16 is supported by a table 18 that can move horizontally. As shown in FIGS. 2 and 5, the transferring mechanism 17 has an arm 21 that swings up to 90 degrees around a shaft 19 by a cylinder 20. A chuck 22 is provided at the other end of the arm 21, and a tube 30 is held by the chuck 22. The structure and the form of chuck 22 is arbitrary. In this embodiment a rubber part is inserted into the open end of a tube 30, and then the rubber part is expanded by pressurized air so that a tube 30 is held by the friction force between the rubber part expanded and the portion of the tube in contact with the rubber part. The arm 21 can move upward and downward by an elevating mechanism 23.

It will now be explained how to test a tube for its strength to resist internal pressure by the apparatus according to the present invention.

First, many tubes 30 are arranged in rack 16. Then an arm 21 in the transferring mechanism 17 is moved over the rack 16, and a tube 30 is picked up with chuck 22.

Secondly, the tube 30 is transferred to a place just above holder 12 by swinging the arm 21 by 90 degrees. At this time holder 12 is set in a low position as shown in FIG. 1. Then holder 12 is elevated by rolling feed screw 14 to hold the tube 30 as shown in FIG. 4. The chuck 22 in arm 21 releases tube 30, and arm swings back over rack 16.

Thirdly, holder 12 that holds tube 30 further elevates so that tube 30 reaches test head 4 in the test position as shown in FIG. 3. At the same time expandable elastomer 5 is inserted into the tube 30. Then, as disclosed before, fluid under a specific pressure provided by open cavity 10 in main body 8 fills the inside of the expandable elastomer 5 through holes of rigid tube 9 to expand the expandable elastomer 5 and to exert a specific internal pressure to the tube 30. A tube 30 that does not stand the pressure is destroyed, and a tube 30 that passes the test remains as it is. A plastic sheet 11 prevents the upper part of an expandable elastomer 5 from unevenly expanding, and thus prevents a tube 30 from being pushed in one direction to result in to a part close to the open end of a tube.

After the test, holder 12 climbs down to a certain extent so that the chuck 22 in arm 21 in the transferring mechanism holds the tube 30 in holder 12. Then holder 12 climbs down further, and arm 21 returns the tube to the rack 16. Then a table 18 is moved so that the arm 21 can pick up another tube 30.

When through testing many tubes a test head 4 wears or an expandable elastomer 5 deteriorates its elasticity, a test head 4 provided with pressurized fluid in a waiting position can promptly replace the test head 4 in the test position by rotating rotary table 2. In this way tests can be continued with minimum interruption.

The apparatus according to the present invention can automatically and continuously test numerous tubes for its strength to resist internal pressure, overcoming disadvantages of the non-automatic, non-continuous apparatus previously disclosed. In addition to this feature, the apparatus as defined in claim 2 prevents potential damage in an area close to the open end of a tube to be tested by a plastic sheet surrounding an upper part of an expandable elastomer. Moreover, the apparatus in claim 3 enables a test head 4 with an expandable elastomer to be smoothly replaced with another test head 4 with an expandable elastomer with minimum interruption in a testing operation.

What is claimed is:

1. An apparatus for testing a tube for its strength to resist internal pressure, comprising:
   at least one expandable elastomer having a hollow body with one open end;
   first means, connected to said at least one expandable elastomer, for providing said at least one expandable elastomer with pressure using fluid as a medium;
   second means for moving a tube into a place in which said at least one expandable elastomer is inserted into a tube at a test position of the apparatus;
   third means, disposed beside said second means, for providing said second means with a tube from a rack; and
   a plastic sheet, connected to said first means, surrounding an upper part of said at least one expandable elastomer.

2. An apparatus as recited in claim 1, further comprising:
   fourth means, connected to said first means, for replacing said first means in the test position with fifth means for providing said at least one expandable elastomer with pressure;
   wherein the apparatus has at least two expandable elastomers; and
   wherein said at least two expandable elastomers are respectively connected to said first and fifth means.

3. An apparatus as recited in claim 2, wherein:
   said first means comprises a main body having an open cavity, said mean body being connected to each of said at least two expandable elastomers in such a way that said open cavity is connected to the open end in each of said at least two expandable elastomers, said main body being connected to said fourth means; and
   said second means comprises a vertical feed screw, a holder for holding a tube movably connected to said vertical feed screw, and means for providing said vertical feed screw with driving force.

* * * * *